US00PP29272P3

(12) United States Plant Patent
Kordes

(10) Patent No.: US PP29,272 P3
(45) Date of Patent: May 8, 2018

(54) HYBRID TEA ROSE PLANT NAMED 'KORVUEBELL'

(50) Latin Name: *Rosa hybrida*
Varietal Denomination: KORvuebell

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 31 days.

(21) Appl. No.: 14/999,142

(22) Filed: Apr. 1, 2016

(65) Prior Publication Data

US 2017/0290218 P1 Oct. 5, 2017

(51) Int. Cl.
*A01H 5/02* (2018.01)

(52) U.S. Cl.
USPC ..... Plt./130
CPC ..... *A01H 5/0222* (2013.01)

(58) Field of Classification Search
USPC ..... Plt./140, 108, 151, 139, 130
CPC ..... A01H 5/0222; A01H 5/0216; A01H 5/02; A01H 5/00
See application file for complete search history.

(56) References Cited

PUBLICATIONS

Help Me Find Roses, Clematis and Peonies 2017 for Gypsy Soul Rose retrieved on Jun. 14, 2017, retrieved from the Internet at <https://www.helpmefind.com/rose/l.php?l=2.73807.2> one page.*

* cited by examiner

*Primary Examiner* — June Hwu
(74) *Attorney, Agent, or Firm* — Samuel R. McCoy, Jr.

(57) ABSTRACT

'KORvuebell' is a new and distinct variety of *Rosa hybrida* which is characterized by the combination of an upright growth habit, dark green and glossy foliage, a high degree of resistance to common rose diseases, and very-double violet-red flowers with strong fragrance. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORvuebell'.

STATEMENT REGARDING PRIOR DISCLOSURES BY THE INVENTOR UNDER 37 C.F.R. 1.77(B)(6)

The first public disclosure of the claimed plant was made by the breeder at a Baden Rose Garden event in Baden-Baden, Germany on Jun. 16, 2015. The claimed plant was first offered for sale on Sep. 20, 2015 in the inventor's mail order catalog. 'KORvuebell' was not publically available or sold prior to one year before the date of the instant application.

BACKGROUND OF THE INVENTION

Parentage: The *Rosa hybrida* variety 'KORvuebell' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform growth and flowering; and
2. Abundant, recurrent violet-red flowers; and
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORvuebell' from all other varieties known to the inventor.

'KORvuebell' is a seedling selection which resulted from the controlled pollination of an unnamed *Rosa hybrida* seedling developed and owned by the same inventor, the seed parent, and *Rosa hybrida* 'KORpauvio' (U.S. Pat. No. 23,495), the pollen parent, during the summer of 2006. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2007 from the seedling beds due to its superior characteristics and asexually propagated for further evaluation. This new and distinctive rose variety was given the name 'KORvuebell'.

Asexual Reproduction: 'KORvuebell' was first asexually propagated by bud grafting in July of 2007 at the inventor's nursery in Klein Offenseth-Sparrieshoop, Germany. Subsequently, 'KORvuebell' has been successfully propagated by stem cuttings and bud grafting in Jackson County, Oreg. These initial and other subsequent propagations conducted in controlled environments demonstrate that 'KORvuebell' reproduces true to type in successive generations of asexual reproduction.

SUMMARY OF THE INVENTION

The following characteristics have been repeatedly observed and represent the distinguishing characteristics of the new *Rosa hybrida* cultivar 'KORvuebell'. These traits, in combination, distinguish 'KORvuebell' as a new and distinct cultivar.

1. *Rosa hybrida* 'KORvuebell' exhibits an upright growth habit; and
2. *Rosa hybrida* 'KORvuebell' exhibits dark green and very glossy foliage; and
3. *Rosa hybrida* 'KORvuebell' exhibits a high degree of resistance to rust, black spot disease, *Botrytis* and powdery mildew; and
4. *Rosa hybrida* 'KORvuebell' exhibits solitary violet-red flowers held upright; and
5. *Rosa hybrida* 'KORvuebell' exhibits very-double flowers of medium size for a hybrid tea rose; and
6. *Rosa hybrida* 'KORvuebell' exhibits flowers with a moderate floral fragrance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORvuebell', taken from a one year old plant.

DETAILED BOTANICAL DESCRIPTION

The following is a detailed botanical description of a new and distinct variety of *Rosa hybrida* known as 'KORvuebell', based upon observations made in August of 2015 from one year old plants grown outdoors in Jackson County, Oreg. Those skilled in the art will appreciate that certain characteristics will vary with older or, conversely, with younger plants. 'KORvuebell' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORvuebell' and comparisons with other varieties of *Rosa hybrida* are provided below.

General plant description:

*Commercial classification.*—Hybrid tea rose.

*Growth rate.*—Moderately vigorous.

*Growth habit.*—Upright.

*Mature dimensions.*—100 cm tall and 80 cm wide, on average.

*Cold hardiness.*—Grown successfully in USDA Hardiness Zones 5 through 9.

*Propagation.*—Stem cuttings and bud grafting.

*Disease resistance.*—Excellent resistance to powdery mildew (*Sphaerotheca pannosa*), blackspot (*Diplocarpon rosae*), rust (both *Phragmidium mucronatum* and *P. tuberculatum*) and *Botrytis cinerea* diseases under normal growing conditions in Jackson County, Oreg.

Root system: Fibrous.

Stems:

*Stem color.*—Young stems are Yellow-Green Group 144A; mature stems are Yellow-Green Group 146A.

*Anthocyanin intonations.*—Greyed-Purple Group 184B intonations are present on young stems.

*Stem surface texture.*—Young stems are smooth while mature stems exhibit a rough texture.

*Stem dimensions.*—Typical mature stems are approximately 400 mm long and 5 mm in diameter.

*Prickles.*—Incidence — Typically 6 prickles per 10 cm of stem on young wood, and 3 prickles per 10 cm of stem on mature stems, on average. Size — Average length is 4 mm long. Immature prickle color — Yellow-Green Group 145C. Mature prickle color — Yellow-Green Group 145C and senescing to Greyed-Orange Group 177B. Anthocyanin intonations — Intonations of Greyed-Purple Group 184B are present on both immature and mature prickles. Shape — Deeply concave. Texture — Smooth.

Leaves:

*Arrangement.*—Imparipinnate compound leaves; mature axillary leaves consisting of 7 leaflets.

*Attachment.*—Petiolate.

*Dimensions.*—170 mm long and 120 mm wide.

*Abundance.*—Average.

*Stipules.*—Size — 25 mm long and 7 mm wide. Stipule color — Yellow-Green Group 146C. Anthocyanin intonations — Intonations of Greyed-Red Group 182B are present on stipitate glands and on the adaxial surface of the midrib. Stipitate glands — A limited number of stipitate glands are present on the margins only. Margins — Glandular toothed. Texture, adaxial surfaces — Glabrous. Texture, abaxial surfaces — Glabrous. Apex — Apiculate. Base — Winged.

*Petiole.*—Length — Average 25 mm. Diameter — Average 1.5 mm. Petiole color, adaxial surface — Yellow-Green Group 146B. Petiole color, abaxial surface — Yellow-Green Group 144A. Anthocyanin intonations — Intonations of Greyed-Red Group 182A are occasionally present on the adaxial surface of the midrib. Margins — Entire. Prickles — None present. Stipitate glands — A limited number of stipitate glands are present on the margins only. Texture and pubescence — Smooth and glabrous. Strength — Moderately strong.

*Rachis.*—Length — Average 25 mm. Diameter — Average 2 mm. Color — Yellow-Green Group 146C. Anthocyanin intonations — Intonations of Greyed-Purple Group 184B are present on the adaxial surface of the midrib. Margins — Entire with a limited number of stipitate glands. Prickles — None present. Stipitate glands — A limited number of stipitate glands are present on the margins only. Texture and pubescence — Smooth and glabrous.

*Leaflets.*—Dimensions — Average size of the terminal leaflet is 65 mm long and 42 mm wide. Shape — Elliptic. Apex — Acute. Base — Obtuse. Margins —

Serrated; not undulated. Luster and texture, adaxial surface — Glossy and leathery. Luster and texture, abaxial surface — Matte and leathery. Juvenile foliage color, adaxial surface — Yellow-Green Group 146A. Juvenile foliage color, abaxial surface — Yellow-Green Group 146C. Mature foliage color, adaxial surface — Yellow-Green Group 147A. Mature foliage color, abaxial surface — Yellow-Green Group 148B. Anthocyanin intonations — Intonations of Greyed-Purple Group 187B cover the juvenile foliage; these same intonations are present on the margins, midrib and entire abaxial surface of intermediate foliage; no anthocyanin intonations are present on mature foliage. Venation — Reticulate. Petiolule — Dimensions — 4 mm long and 1 mm in diameter. Petiolule color, adaxial surface — Yellow-Green Group 145A. Petiolule color, abaxial surface — Yellow-Green Group 145A. Anthocyanin intonations — Intonations of Greyed-Purple Group 183B are present on the margin of the adaxial surface. Prickles — None present. Texture, adaxial and abaxial surfaces — Smooth. Margins — Entire, with a limited number of stipitate glands present.

Inflorescence:

*Inflorescence type.*—Peduncles give rise to solitary flowers. Flowers are held upright.

*Blooming habit.*—Recurrent; floriferous.

*Size.*—50 mm tall and 90 mm wide, on average.

*Peduncle.*—Length — 15 to 30 mm average length. Diameter — 2 to 3.5 mm average diameter. Color — Yellow-Green Group 146C. Anthocyanin intonations — Intonations of Greyed-Orange Group 177B to Greyed-Red Group 178A present on the distal portion of the peduncle. Strength — Strong. Texture and pubescence — Smooth and glabrous.

Flowering laterals: Absent.

Bud:

*Bud form.*—Long; globular.

*Size.*—Upon opening, 25 mm in length from base of receptacle to distal end of bud and 25 mm diameter at its widest point.

*Texture.*—Coriaceous; leathery, stiff and tough but somewhat flexible.

*Color, as sepals first unfold.*—Greyed-Purple Group 187A.

*Color when one-quarter open, inner side.*—Marginal zone — Red-Purple Group 59B. Middle zone — Red-Purple Group 59B. Basal zone — Red-Purple Group 59B with intonations of White Group 155B. Basal spot — White Group 155B; approximately 2 mm long and 3 mm wide.

*Color when one-quarter open, outer side.*—Marginal zone — Red-Purple Group 60C. Middle zone — Red-Purple Group 60C. Basal zone — Red-Purple Group 60C.

*Color when one-quarter open, outermost petals.*—Typically one outermost petal is observed with intonations of Green-Yellow Group 145B and 145C across the petal.

Flower:

*Calyx.*—General — Comprised of five polysepalous sepals, with moderate foliaceous appendages present on three of the five sepals. Diameter of calyx — 8 mm, at anthesis. Sepals — Color, upper surface — Yellow-Green Group 146C. Color, lower surface — Yellow-Green Group 146C. Anthocyanin intonations — Greyed-Orange Group 177B to Greyed-Red Group 178A. Size — 25 mm long and 8 mm wide, on average. Apex — Cirrose. Base — Flat at union with receptacle. Quantity — Five. Upper surface — Pubescent. Lower surface — Lightly pubescent, with a limited number of stipitate glands. Margins — Pubescent with stipitate glands present at the apex.

*Corolla.*—General shape of corolla — Rosette; round. Shape of corolla when viewed from the side — Upon opening, upper portion — Flattened convex. Upon opening, lower portion — Flat. Open flower, upper portion — Concave. Open flower, lower portion — Convex. Dimensions — Medium size for a hybrid tea rose. When open, the average flower diameter is 100 mm and the average flower height is 65 mm. Fragrance — Moderate floral fragrance. Duration — On the plant for 4 to 5 days; as a cut flower, flowers will last 3 to 4 days. Senesced petals drop away cleanly. Petals — Petal count — Exhibits very double flowers with an average of 70 petals under normal conditions. Petal reflex — Petals are somewhat reflexed. Timing of petal reflex — Simultaneous. Petal margin — Entire to slightly ruffled. Petal shape — Obovate. Apex — Obtuse. Base — Obtuse. Dimensions — 30 to 40 mm long and 20 to 30 mm wide. Texture, inner surface — Smooth. Texture, outer surface — Smooth. Petal color, upon opening — Outermost petals, inner surface — Red-Purple Group 59C. Outermost petals, outer surface — Red-Purple Group 59A to 59B. Innermost petals, inner surface — Red-Purple Group 60A. Innermost petals, outer surface — Red-Purple Group 60C. Basal petal spots, upon opening — Outermost petals — Color, inner surface — White Group 155A. Color, outer surface — No distinct petal spot. Dimensions — 3 mm high and 3 mm wide. Innermost petals, inner surface — Color, inner surface — White Group 155A. Color, outer surface — No distinct petal spot. Dimensions — 2 mm high and 2 mm wide. Petal color, after opening — Outermost petals, inner surface — Red-Purple Group 59C. Outermost petals, outer surface — Red-Purple Group 60C. Innermost petals, inner surface — Red-Purple Group 61B. Innermost petals, outer surface — Red-Purple Group 64B. Basal petal spots, after opening — Outermost petals, inner surface — Color, inner surface — White Group 155A. Color, outer surface — White Group 155A. Dimensions — 5 mm high and 3 mm wide. General Tonality — On open flower, Red-Purple Group 59C. No change in general tonality at the end of the third day; thereafter the general tonality is Red-Purple Group 60C. Petaloids — Quantity — 20 petaloids per flower, on average. Dimensions — Approximately 10 to 30 mm long and 5 to 15 mm wide. Color, inner surface — Red-Purple Group 60C. Color, outer surface — Red-Purple Group 60A. Margins — Entire to undulated. Shape — Irregular; oblanceolate to obovate. Apex — Obtuse. Base — Attenuate. Texture, inner and outer surfaces — Smooth.

Reproductive organs:

*Stamens.*—Quantity — Approximately 45, on average, and regularly arranged around the styles. Anthers — Shape — Reniform. Dimensions — 3 mm long and 1 mm wide, on average. Color — Yellow Group 4B. Pollen — Present; moderate. Color is Greyed-Orange Group 163C. Filaments — Color — Yellow-Green Group 145C at the base and transitioning to Red Group 50C on the distal two-thirds of the filament. Length — 4 to 5 mm.

*Pistils.*—Quantity — Average; approximately 30. Stigmas — Dimensions — 2 mm long and 0.5 mm wide. Location — Superior in position to anthers. Color — Red Group 47B. Styles — Length — Approximately 5 mm long. Color — Red Group 53C.

*Ovary.*—Dimensions — 8 mm long and 4 mm in diameter. Color — White Group 155C.

*Receptacle.*—Shape — Urn-shaped. Dimensions — Approximately 10 mm high and 8 mm wide. Surface texture and pubescence — Generally smooth, with occasional stipitate glands. Color — Yellow-Green Group 144B, with intonations of Greyed-Red Group 181B at the base. Texture — Glabrous.

Hips and seed formation: Not observed to date.

Comparisons with the Parents

The new rose plant may be distinguished from its seed parent, a *Rosa hybrida* breeding line developed by the inventor, by the following combination of characteristics:

1. 'KORvuebell' exhibits red-purple flowers, whereas the seed parent exhibits medium-red flowers.
2. 'KORvuebell' exhibits a very double petal count, whereas the seed parent exhibits a semi-double petal count.
3. 'KORvuebell' exhibits high disease resistance, whereas the seed parent exhibits very high disease resistance.

The new rose plant may be distinguished from its pollen parent, *Rosa hybrida* 'KORpauvio', by the following combination of characteristics:

1. 'KORvuebell' exhibits very glossy foliage, whereas 'KORpauvio' exhibits semi-glossy foliage.
2. 'KORvuebell' exhibits red-purple flowers, whereas 'KORpauvio' exhibits medium-pink flowers.
3. 'KORvuebell' exhibits moderate fragrance, whereas 'KORpauvio' exhibits strong fragrance.

Comparison with the Most Similar *Rosa* Cultivar Known to the Inventor

For a comparison, several physical characteristics of the *Rosa hybrida* variety 'KORcoluma', a rose variety from the same inventor which is described and illustrated in U.S. Pat. No. 17,047, are compared to 'KORvuebell' in Chart 1.

CHART 1

| Characteristic | 'KORvuebell' | 'KORcoluma' |
|---|---|---|
| General tonality of the flower, at anthesis. | Red-Purple Group 60C. | Red Group 46B. |
| Average diameter of the corolla, at anthesis. | 100 mm. | 80 to 100 mm. |
| Fragrance. | Moderate. | Light to moderate. |

The invention claimed is:

1. A new and distinct variety of rose plant named 'KORvuebell', as described and illustrated herein.

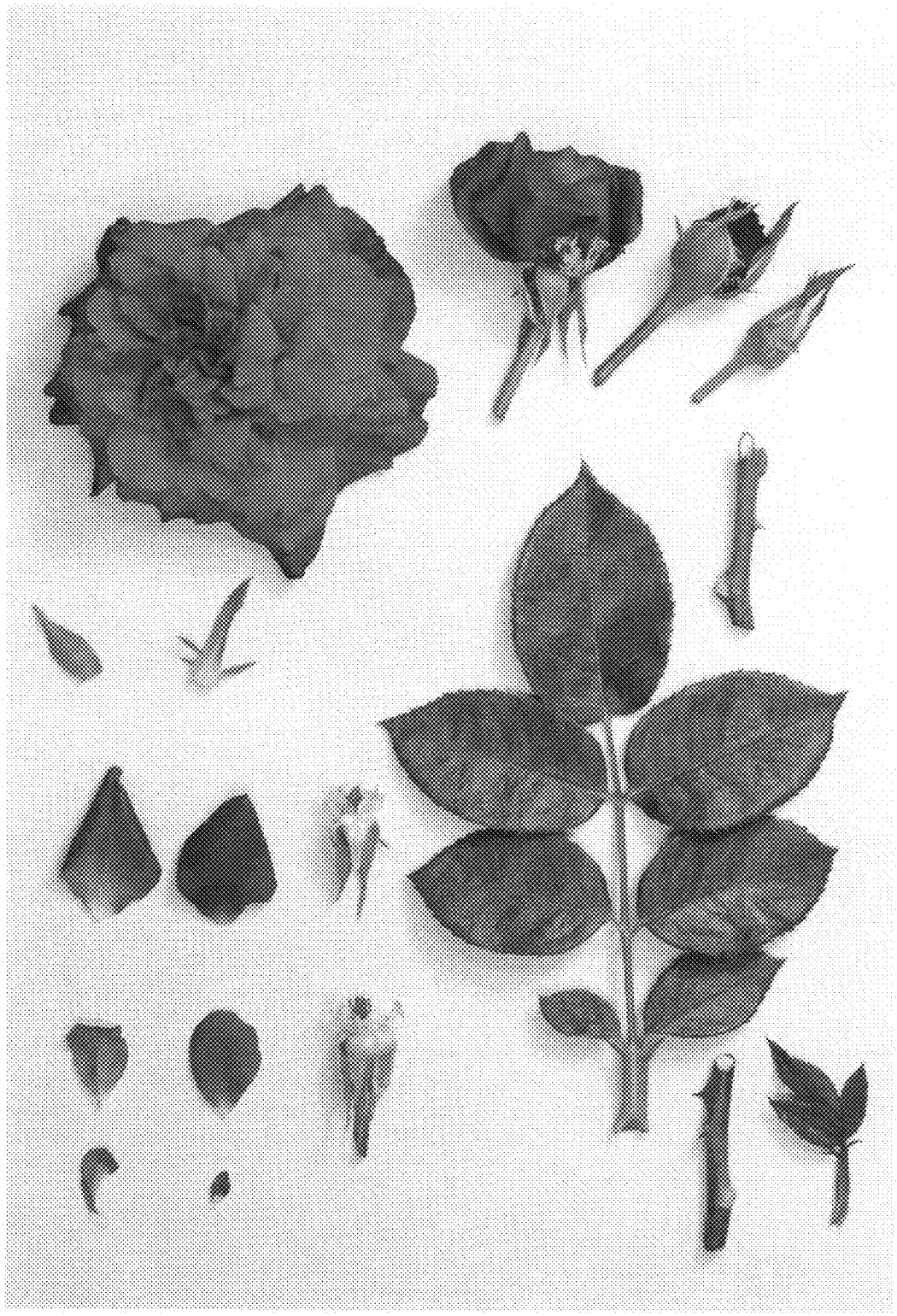

* * * * *